(12) United States Patent
Balicki et al.

(10) Patent No.: US 12,274,580 B2
(45) Date of Patent: Apr. 15, 2025

(54) SYSTEMS AND METHODS FOR GUIDING AN ULTRASOUND PROBE

(71) Applicant: KONINKLIJKE PHILIPS N.V., Eindhoven (NL)

(72) Inventors: Marcin Arkadiusz Balicki, Cambridge, MA (US); Paul Thienphrapa, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 36 days.

(21) Appl. No.: 17/783,380

(22) PCT Filed: Dec. 12, 2020

(86) PCT No.: PCT/EP2020/085869
§ 371 (c)(1),
(2) Date: Jun. 8, 2022

(87) PCT Pub. No.: WO2021/116474
PCT Pub. Date: Jun. 17, 2021

(65) Prior Publication Data
US 2022/0409292 A1  Dec. 29, 2022

Related U.S. Application Data

(60) Provisional application No. 62/947,162, filed on Dec. 12, 2019.

(51) Int. Cl.
*A61B 1/00* (2006.01)
*A61B 1/05* (2006.01)
(Continued)

(52) U.S. Cl.
CPC .......... *A61B 8/12* (2013.01); *A61B 1/000094* (2022.02); *A61B 1/0016* (2013.01);
(Continued)

(58) Field of Classification Search
CPC ..... A61B 8/12; A61B 34/20; A61B 1/000094; A61B 1/0016; A61B 1/05; A61B 1/273;
(Continued)

(56) References Cited

U.S. PATENT DOCUMENTS 5,906,578 A  5/1999 Rajan
8,303,505 B2  11/2012 Webler
(Continued)

FOREIGN PATENT DOCUMENTS

JP  2008036447 A  2/2008
JP  5118455 B2  1/2013

OTHER PUBLICATIONS

International Search Report and Written Opinion Dated Apr. 15, 2021 for International Application No. PCT/EP2020/085869 Filed Dec. 12, 2020.
(Continued)

*Primary Examiner* — Sean A Frith

(57) ABSTRACT

An ultrasound device (10) includes a probe (12) including a tube (14) sized for insertion into a patient and an ultrasound transducer (18) disposed at a distal end (16) of the tube. A camera (20) is mounted at the distal end of the tube in a fixed spatial relationship to the ultrasound transducer. At least one electronic processor (28) is programmed to: control the ultrasound transducer and the camera to acquire ultrasound images (19) and camera images (21) respectively while the ultrasound transducer is disposed in vivo inside the patient; and construct a keyframe (36) representative of an in vivo position of the ultrasound transducer including at least ultrasound image features (38) extracted from at least one of the ultrasound images acquired at the in vivo position of the ultrasound transducer and camera image features (40) extracted from one of the camera images acquired at the in vivo position of the ultrasound transducer.

19 Claims, 6 Drawing Sheets

(51) Int. Cl.
  *A61B 1/273* (2006.01)
  *A61B 8/00* (2006.01)
  *A61B 8/08* (2006.01)
  *A61B 8/12* (2006.01)
  *A61B 34/20* (2016.01)

(52) U.S. Cl.
  CPC ............... *A61B 1/05* (2013.01); *A61B 1/273* (2013.01); *A61B 8/4254* (2013.01); *A61B 8/4416* (2013.01); *A61B 8/445* (2013.01); *A61B 8/463* (2013.01); *A61B 8/467* (2013.01); *A61B 8/5223* (2013.01); *A61B 8/5261* (2013.01); *A61B 8/54* (2013.01); *A61B 34/20* (2016.02); *A61B 2034/2055* (2016.02); *A61B 2034/2063* (2016.02)

(58) Field of Classification Search
  CPC ..... A61B 8/4254; A61B 8/4416; A61B 8/445; A61B 8/463; A61B 8/467; A61B 8/5223; A61B 8/5261; A61B 8/54; A61B 2034/2055; A61B 2034/2063
  See application file for complete search history.

(56) References Cited

U.S. PATENT DOCUMENTS

| | | | |
|---|---|---|---|
| 9,717,563 B2* | 8/2017 | Tognaccini | A61B 1/04 |
| 10,045,758 B2 | 8/2018 | Marmor | |
| 10,682,108 B1* | 6/2020 | Ma | A61B 1/000096 |
| 2008/0249407 A1 | 10/2008 | Hill et al. | |
| 2009/0304250 A1 | 12/2009 | McDermott et al. | |
| 2012/0087561 A1* | 4/2012 | Guetter | G06T 7/174 382/131 |
| 2012/0302875 A1* | 11/2012 | Kohring | A61B 1/05 600/424 |
| 2016/0262722 A1* | 9/2016 | Marmor | A61B 8/4254 |
| 2016/0338667 A1* | 11/2016 | Noonan | A61B 8/467 |
| 2017/0258440 A1 | 9/2017 | Marmor | |
| 2018/0185008 A1 | 7/2018 | Andersen | |
| 2019/0008490 A1* | 1/2019 | Greminger | A61B 1/00135 |
| 2019/0015167 A1 | 1/2019 | Draelos | |
| 2019/0261947 A1* | 8/2019 | Themelis | A61B 5/0071 |
| 2019/0336101 A1* | 11/2019 | Chiang | A61B 1/00 |
| 2019/0380676 A1* | 12/2019 | Swan | G16H 30/40 |
| 2020/0323514 A1 | 10/2020 | Thienphrapa et al. | |
| 2020/0367970 A1* | 11/2020 | Qiu | A61B 90/36 |

OTHER PUBLICATIONS

Sonia Nhieu: "Chapter 2, Transesophageal Echocardiography: Essential Views", 2016.

Cardio Command: Optimal Positioning of Electrodes for Transesophageal Atrial Pacing http://www.cardiocommand.com/taptechnology_methods.html.

Pattison, et al: "Atrial pacing thresholds measured in anesthetized patients with the use of an esophageal stethoscope modified for pacing", Journal of Clinical Anesthesia , vol. 9 , Issue 6, 492.

Visura https://www.visuratechnologies.com/.

Mathur, et al: "Transoesophageal Echocardiography Related Complications", Indian Journal of Anaesthesia. 2009;53(5):567-574.

* cited by examiner

SYSTEMS AND METHODS FOR GUIDING AN ULTRASOUND PROBE

CROSS REFERENCE TO RELATED APPLICATIONS

This application is the U.S. National Phase application under 35 U.S.C. § 371 of International Application No. PCT/EP2020/085869 filed Dec. 12, 2020, which claims the benefit of European Patent Application Number 62/947,162 filed Dec. 12, 2019. These applications are hereby incorporated by reference herein.

FIELD

The following relates generally to the ultrasound arts, ultrasound imaging arts, ultrasound probe arts, ultrasound probe guidance arts, ultrasound catheter arts, transesophageal echography (TEE) arts, and related arts.

BACKGROUND

Ultrasound imaging employing an ultrasound transducer array mounted on the end of an insertion tube, and in particular transesophageal echocardiography (TEE), is an existing imaging methodology with various uses, most commonly for diagnostic purposes for cardiac patients and for providing image guidance during catheter-based cardiac interventional procedures. TEE involves an approach for cardiac ultrasound imaging in which the ultrasound probe includes a cable or tube with the ultrasound transducer located at its tip. The TEE probe is inserted into the esophagus to place the ultrasound transducers at its distal tip close to the heart.

In catheter-based structural heart interventions TEE has been widely adapted as a reliable approach to imaging the interventional catheter instrument used in treating structural heart disease. Three-dimensional (3D) trans-esophageal ultrasound (US) is used for interventional guidance in catheter-lab procedures since it offers real-time volumetric imaging that enhances visualization of cardiac anatomy, compared to two-dimensional (2D) slice visualization with B-mode ultrasound, and provides exceptional soft tissue visualization, which is missing in x-ray. For many structural heart disease (SHD) interventions (e.g., mitral valve replacement), TEE is commonly used.

Typically, a TEE probe is inserted into the esophagus by a trained sonographer (or cardiologist) and is adjusted manually towards a number of standard viewing positions such that a particular anatomy and perspective of the heart is within the field of view of the US device. Different measurements or inspections might require different field of views/perspectives of the same anatomy, in which case the probe needs to be re-positioned. During interventions, the probe is often moved between view positions in order to accommodate X-Ray imaging as well as tracking the progress of the intervention as the device is maneuvered. Sometimes, the probe is moved incidentally due to physiological motion, or inadvertently due to other reasons, and must be restored to a desired view position.

TEE probes typically include cable-driven mechanical joints at the distal end of the probe that can be manually operated by knobs on a handle of the TEE probe. The distal dexterity provided by these joints, along with manually controlled rotation and insertion distance of the TEE probe, and electronic beam steering of the ultrasound imaging plane(s), provides substantial flexibility in positioning the ultrasound transducer and the imaging plane so as to acquire a desired view of the heart. However, concerns include a risk of perforating the esophagus, and difficulty in manipulating the many degrees of control to achieve a desired clinical view, and TEE operator's exposure to harmful radiation from the x-ray source during interventions.

In addition to TEE, other types of ultrasound imaging that employ a probe having a tube sized for insertion into a patient (i.e. a catheter) with an ultrasound transducer disposed at the distal end of the tube include: Intracardiac Echo (ICE) probes which are usually thinner than TEE probes and are inserted into blood vessels to move the ultrasound transducer array inside the heart; and Intravascular Ultrasound (IVUS) probes which are also thin and are inserted into blood vessels to image various anatomy from interior vantage points.

The following discloses certain improvements to overcome these problems and others.

SUMMARY

In one aspect, an ultrasound device includes a probe including a tube sized for insertion into a patient and an ultrasound transducer disposed at a distal end of the tube. A camera is mounted at the distal end of the tube in a fixed spatial relationship to the ultrasound transducer. At least one electronic processor is programmed to: control the ultrasound transducer and the camera to acquire ultrasound images and camera images respectively while the ultrasound transducer is disposed in vivo inside the patient; and construct a keyframe representative of an in vivo position of the ultrasound transducer including at least ultrasound image features extracted from at least one of the ultrasound images acquired at the in vivo position of the ultrasound transducer and camera image features extracted from one of the camera images acquired at the in vivo position of the ultrasound transducer.

In another aspect, an ultrasound device comprises a probe including a tube sized for insertion into a patient and an ultrasound transducer disposed at a distal end of the tube and arranged to be side-emitting. A camera is mounted at the distal end of the tube in a fixed spatial relationship to the ultrasound transducer and arranged to be forward-facing. At least one electronic processor is programmed to: control the ultrasound transducer and the camera to acquire ultrasound images and camera images respectively while the ultrasound transducer is disposed in vivo inside the patient; and construct a keyframe representative of an in vivo position of the ultrasound transducer including at least ultrasound image features extracted from at least one of the ultrasound images acquired at the in vivo position of the ultrasound transducer and camera image features extracted from one of the camera images acquired at the in vivo position of the ultrasound transducer.

In another aspect, a method of controlling an ultrasound device that comprises a probe including a tube sized for insertion into a patient and an ultrasound transducer disposed at a distal end of the tube and a camera mounted at the distal end of the tube in a fixed spatial relationship to the ultrasound transducer is disclosed. The method includes: controlling the ultrasound transducer and the camera to acquire ultrasound images and camera images respectively while the ultrasound transducer is disposed in vivo inside the patient; constructing a keyframe representative of a first view consisting of a first in vivo position of the ultrasound transducer, the keyframe including at least the ultrasound images, the camera images, ultrasound image features extracted from at least one of the ultrasound images acquired at the in vivo position of the ultrasound transducer and camera image features extracted from one of the camera images acquired at the in vivo position of the ultrasound transducer; during a traversal of the ultrasound transducer from the first view to a second view consisting of a second in vivo position of the ultrasound transducer, constructing keyframes representative of intermediate positions of the ultrasound transducer; and at the end of the traversal, constructing a keyframe representative the second view.

One advantage resides in providing proper positioning of an ultrasound probe to acquire cardiac images at specific views.

Another advantage resides in providing an ultrasound probe with multiple image devices to acquire cardiac images.

Another advantage resides in providing an ultrasound probe that provides feedback to a user for maneuvering the ultrasound probe.

Another advantage resides in providing an ultrasound probe with less operational complexity, reducing errors and costs.

Another advantage resides in providing an ultrasound probe with servomotors that automatically maneuver the ultrasound probe through an esophagus, blood vessel, or other anatomy having a traversable lumen.

Another advantage resides in reducing x-ray exposure to an operator of an ultrasound device by actuating the ultrasound probe to be controlled remotely and/or automatically.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
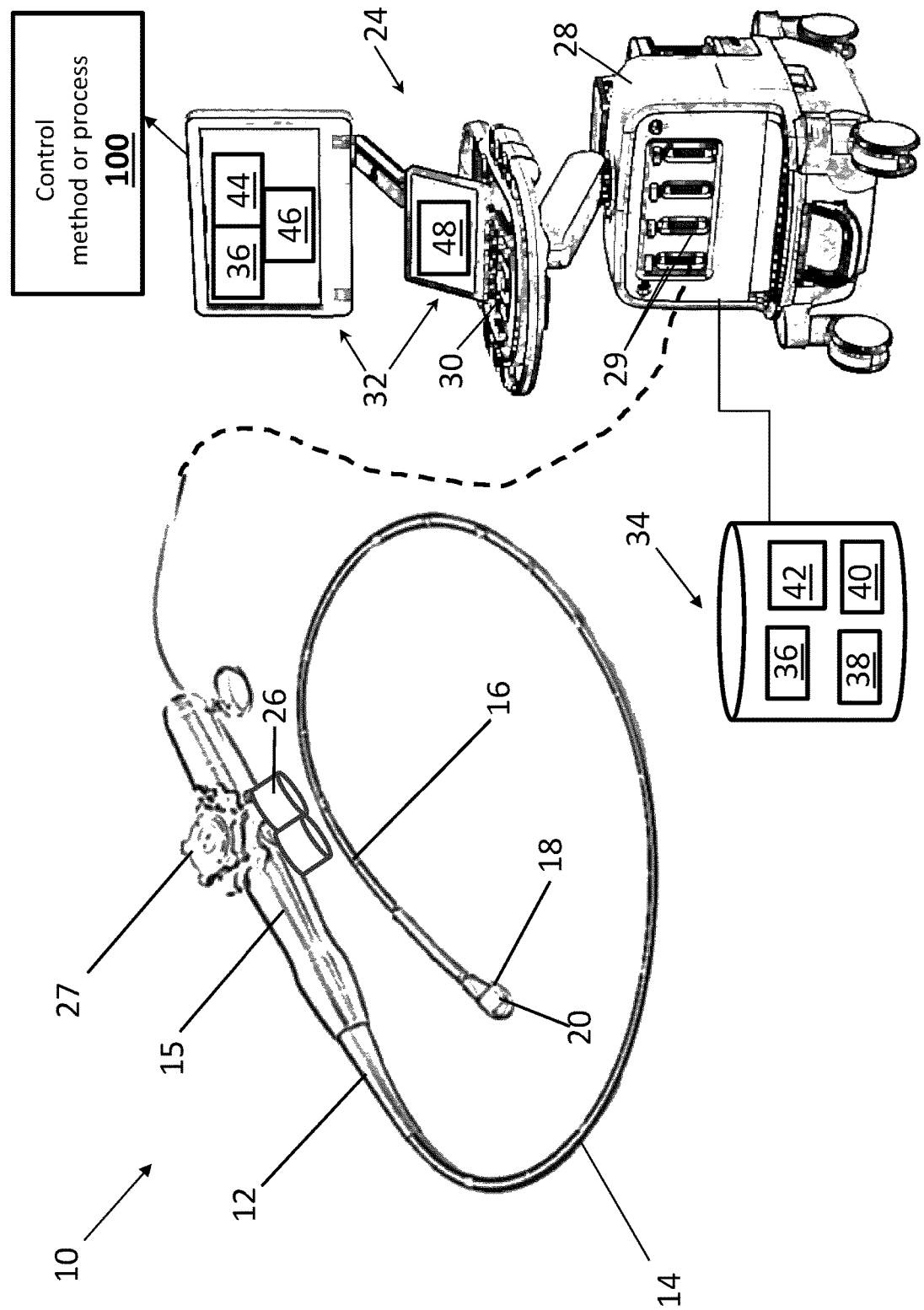
FIGS. 1 and 2 illustrate an exemplary embodiment of an ultrasound device in accordance with one aspect.

The systems and methods disclosed herein provide for keyframes. As used herein, a keyframe (and variants thereof) refer to an image signature representing a particular position of a TEE probe (or other catheter-based ultrasound probe). It is recognized herein that ultrasound images alone can be insufficient for generating reliable keyframes, because the ultrasound imaging can be intermittent and provides a relatively low-resolution image. To provide more robust keyframes, a video camera is integrated into the probe tip, attached with the ultrasound transducer or positioned closely thereto on the probe so as to move together.

In a typical workflow, the TEE probe acquires keyframes at points along the traversal of the esophagus. For example, a new keyframe may be acquired each time the image loses (due to movement and/or electronic beam steering) more than a threshold fraction of image features (e.g. in an ultrasound image or a camera image). Optionally, when the physician reaches a desired view a manual acquisition of a keyframe may be acquired and labeled with the view. Alternatively, the view may be recognized automatically based on image analysis automatically identifying defining image features, and the corresponding keyframe labeled with the view. It can also be defined by a dwell time, where there is no major motion change of the probe. If the physician then wants to return to a previous view, the servo motor is reversed to move the probe tip backwards, and the acquired images are compared with key points along the way to automatically trace and adjust (if needed) the backtracking traversal process. In other embodiments, the servo motor is moved via a sequence of servo motions corresponding to keyframe transitions that link a current view to a desired view. In some examples, visual servo methods supplement open loop motion from keyframe to keyframe. The keyframe motion includes (but is not limited to) physical motion of the probe and electronic beam steering. The motion can also include imaging settings (e.g., ultrasound parameters, camera settings, and so forth).

In some embodiments disclosed herein, a manual mode is implemented. In this case, the TEE probe is a manually operated probe having knobs for controlling the joints of the TEE probe, and the system provides control prompts such as "advance insertion", "retract", 'rotate', 'flex', "at view", or so forth based on the feedback obtained by comparing real-time images with previously acquired keyframes. In other embodiments, the TEE probe is partly or completely robotic, with servomotors replacing the mechanical manipulation to operate the TEE probe, such as distal joint control, insertion, rotation, etc. In this case, the system can directly control the servomotors to execute the desired TEE probe manipulations. The system can also control ultrasound imaging parameters (e.g., imaging depth, beam steering angle, gains, etc.) to recall previous settings for a given view.

In some embodiments disclosed herein, the ultrasound transducer is side-emitting while the video camera is forward looking, which is a convenient arrangement as a side-emitting ultrasound transducer is well-placed to image the heart, while the forward-looking video camera provides a vantage that is not provided by the side-emitting transducer. Of particular value, a forward-looking camera can detect an obstruction that would prevent further insertion of the TEE probe, and can visualize the appropriate action (e.g. turning of a probe joint) to avoid collision with the obstruction.

Figure 2:
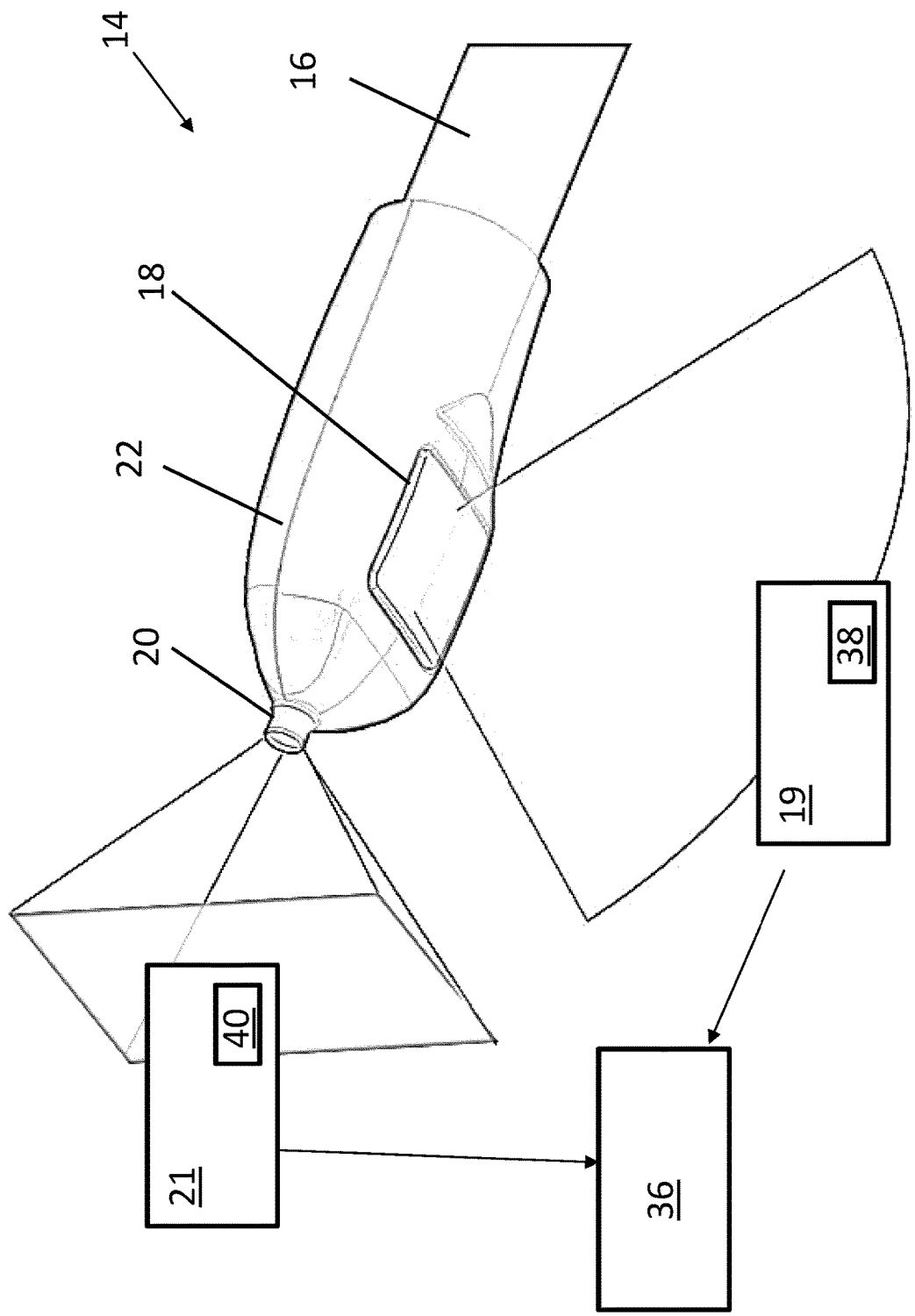

FIGS. 1 and 2 illustrate one exemplary embodiment of an ultrasound device 10 for a medical procedure, in particular a cardiac imaging procedure. Although referred to herein as a TEE ultrasound device, the ultrasound device 10 may be any suitable catheter-based ultrasound device (e.g., an ultrasound device for an intracardiac echo (ICE) procedures, intravascular US procedures, among others). As shown in FIG. 1, the ultrasound device 10 includes a probe 12 configured as, for example, a flexible cable or tube that serves as a catheter for insertion into a lumen of the patient (e.g., the lumen may be an esophageal lumen, or a blood vessel lumen, or so forth). The probe 12 can be any suitable, commercially-available probe (e.g., a Philips x7-2 TEE probe, available from Koninklijke Philips N.V., Eindhoven, the Netherlands). As described herein, the probe 12 is described as being used in a TEE procedure including inserting the probe into an esophagus of a patient to acquire images of the patient's heart, it will be appreciated that the probe can be inserted into any portion of the patient to acquire images of any target tissue.

The probe 12 includes a tube 14 that is sized for insertion into a portion of a patient (e.g., an esophagus). The tube 14 can be flexible or rigid. In some examples, the tube 14 has a handle 15 that is disposed outside of the patient and is manipulated by the user. The tube 14 includes a distal end 16 with an ultrasound transducer 18 disposed thereat. The ultrasound transducer 18 is configured to acquire ultrasound images 19 of a target tissue (e.g., a heart or surround vasculature). A camera 20 (e.g., a video camera such as an RGB or other color camera, a monochrome camera, an infrared (IR) camera, a stereo camera, a depth camera, a spectral camera, an optical coherence tomography (OCT) camera, and so forth) is also disposed at the distal end 16 of the tube 14. The camera 20 is configured to acquire camera (e.g., still and/or video) images 21 of the target tissue. The camera 20 can be any suitable, commercially-available camera (such as a camera described in Pattison et al., "Atrial pacing thresholds measured in anesthetized patients with the use of an esophagus stethoscope modified for pacing", Journal of Clinical Anesthesia, Volume 9, Issue 6, 492).

The camera 20 is mounted in a fixed spatial relationship to the ultrasound transducer 18. In one example embodiment, the ultrasound transducer 18 and the camera 20 are attached to each other, or, as shown in FIGS. 1 and 2, housed or otherwise secured to a common housing 22 located at the distal end 16 of the tube 14. In particular, as shown in FIG. 2, the ultrasound transducer 18 is arranged to be side-emitting, and the camera 20 is arranged to be forward-facing. Advantageously, this arrangement as shown in FIG. 1 provides side-emitting ultrasound transducer 18 is well-placed to image the heart, while the forward-looking video camera 20 provides a vantage (e.g., of the heart) that is not provided by the side-emitting transducer. In other example embodiments, the camera 20 can be steerable using robotic actuation, or manually using cables or other means, such as mirror lenses (not shown). In another example, the ultrasound transducer 18 and the camera 20 can be connected by some other mechanism (e.g., a flexible cable) and tracked relative to each other.

The ultrasound device 10 also includes an electronic controller 24, which can comprise a workstation, such as an electronic processing device, a workstation computer, a smart tablet, or more generally a computer. In the non-limiting illustrative example, the electronic controller 24 is a Philips EPIQ class ultrasound workstation. (Note that the ultrasound workstation 24 and the TEE probe 12 are shown at different scales). The electronic controller 24 can control operation of the ultrasound device 10, including, for example, controlling the ultrasound transducer 18 and/or the camera 20 to acquire images, along with controlling movement of the probe 12 through the esophagus by controlling one or more servomotors 26 of the ultrasound device 10 which are connected to drive its articulating joints (not shown) and/or to rotate and/or extend and retract the tube 14. Alternatively, one or more knobs 27 may be provided by which the user manually operates the drive joints to maneuver the probe through the esophagus.

While FIG. 1 shows both knob and servomotor components 26, 27 for illustrative purposes, typically the ultrasound probe 12 will be either manual (having only knobs) or robotic (having only servomotors), although hybrid manual/robotic designs are contemplated, such as a design in which the user manually extends/retracts the tube 14 while servomotors are provided to robotically operate the probe position and its joints.

The workstation 24 includes typical components, such as at least one electronic processor 28 (e.g., a microprocessor) including connectors 29 for plugging in ultrasound probes (a dashed cable is shown in FIG. 1 diagrammatically indicating the TEE probe 12 is connected with the ultrasound workstation 24), at least one user input device (e.g., a mouse, a joystick, a keyboard, a trackball, and/or the like) 30, and at least one display device 32 (e.g. an LCD display, plasma display, heads-up display, augmented reality display, cathode ray tube display, and/or so forth). The illustrative ultrasound workstation 24 includes two display devices 32: a larger upper display device on which ultrasound images are displayed, and a smaller lower display device on which a graphical user interface (GUI) 48 for controlling the workstation 24 is displayed. In some embodiments, the display device 32 can be a separate component from the workstation 24. The display device 32 may also comprise two or more display devices. In some embodiments, the user input device 30 can be a separate component from the workstation 24, and in some cases can be virtual, provided inside an augmented reality system.

The electronic processor 28 is operatively connected with a one or more non-transitory storage media 34. The non-transitory storage media 34 may, by way of non-limiting illustrative example, include one or more of a magnetic disk, RAID, or other magnetic storage medium; a solid state drive, flash drive, electronically erasable read-only memory (EEROM) or other electronic memory; an optical disk or other optical storage; various combinations thereof; or so forth; and may be for example a network storage, an internal hard drive of the workstation 24, various combinations thereof, or so forth. While shown separately from the controller 24, in some embodiments, a portion or all of the one or more non-transitory storage media 34 may be integral with the ultrasound workstation 24, for example comprising an internal hard disk drive or solid-state drive. It is to be further understood that any reference to a non-transitory medium or media 34 herein is to be broadly construed as encompassing a single medium or multiple media of the same or different types. Likewise, the electronic processor 28 may be embodied as a single electronic processor or as two or more electronic processors. The non-transitory storage media 34 stores instructions executable by the at least one electronic processor 28.

The ultrasound device 10 is configured as described above to perform a control method or process 100 for controlling movement of the probe 12. The non-transitory storage medium 32 stores instructions which are readable and executable by the at least one electronic processor 28 of the workstation 24 to perform disclosed operations including performing the control method or process 100. In some examples, the control method 100 may be performed at least in part by cloud processing.

Figure 3:
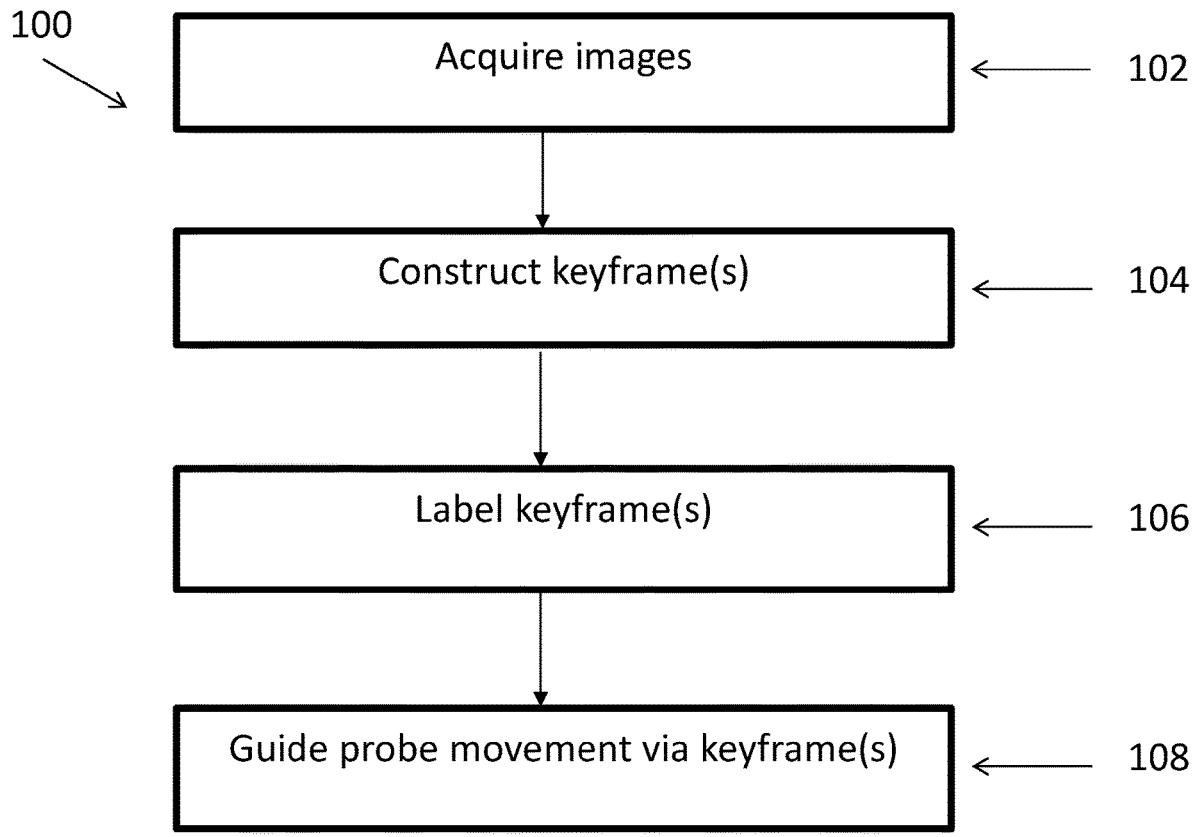
FIG. 3 shows exemplary flow chart operations of the ultrasound device of FIGS. 1 and 2.

Referring now to FIG. 3, and with continuing reference to FIGS. 1 and 2, an illustrative embodiment of the control method or process 100 is diagrammatically shown as a flowchart. At an operation 102, the at least one electronic processor 28 is programmed to control the ultrasound transducer 18 and the camera 20 to acquire ultrasound images 19 and camera images 21 respectively while the ultrasound transducer (and also the camera 20 and the common rigid housing 22) is disposed in vivo inside the esophagus of the patient.

At an operation 104, the at least one electronic processor 28 is programmed to construct a keyframe 36 representative of an in vivo position of the ultrasound transducer 18 (e.g., within the esophagus). To construct the keyframe 36, the at least one electronic processor 28 is programmed to extract ultrasound image features 38 from at least one of the ultrasound images 19, and/or extract camera image features 40 from at least one of the camera images 21. In another example, the keyframes 36 can include the ultrasound images 19 and/or the camera images 21 themselves. The ultrasound images 19 and the camera images 21 can be stored in the one or more non-transitory computer media 34, and/or displayed on the display device 32. The extraction process can include an algorithm to extract feature sets between the at least one ultrasound image feature 38 and the at least one camera image feature 40. Such algorithms can include, for example, a scale-invariant feature transform (SIFT) algorithm, a multi-scale-oriented patches (MOPS), algorithm, a vessel tracking algorithm, or any other suitable matching algorithm known in the art. In a variant embodiment, the operation 102 acquires only ultrasound images using the ultrasound transducer 18 (in which case the camera 20 may optionally be omitted), and the operation 104 constructs the keyframe using features 38 extracted only from the ultrasound images. However, it is expected that constructing the keyframe 36 using features extracted from both the ultrasound image 19 and the camera image 21 will provide the keyframe 36 with a higher level of discriminativeness for uniquely identifying a given view, and moreover the camera image 21 can be useful in situations in which the ultrasound image has low contrast or otherwise has information-deficient features (and vice versa, if the camera image is information-deficient then this is compensated by the features extracted from the ultrasound image).

In one example, the keyframe 36 can further include features comprising one or more settings (e.g., beam steering, depth, resolution, width, and so forth) of the ultrasound transducer 18 at the acquisition time of the ultrasound image 19 from which the image feature 38 is extracted at the in vivo position of the transducer. In another example, the keyframe 36 can include rotation settings and/or insertion settings of the probe 12 and/or joint position settings of the probe at the acquisition time of one or more of the ultrasound images 19 and/or the camera images 21. The joint position settings can include, for example, settings such as "insert," rotate," "flex" and so forth. These settings can be determined from positional feedback devices (not shown), such as encoders) and/or sensor feedback devices (not shown) such as force sensors or torque sensors, related to the shape and location of the probe 12.

In some example embodiments, the operation 104 includes constructing a keyframe 36 responsive to satisfaction of one or more keyframe acquisition criteria 42 (which can be stored in the one or more non-transitory computer readable media 34). In one example, the keyframe acquisition criterion 42 can include a comparison between a "last-acquired" keyframe 36 and currently-acquired ultrasound images 19 and/or currently-acquired camera images 21. In another example, the keyframe acquisition criterion 42 can include a comparison between a keyframe 36 acquired at a preset previous amount of time (e.g., a keyframe acquired, for example, 30 seconds previously) and currently-acquired ultrasound images 19 and/or currently-acquired camera images 21. The keyframes 36 can be stored in the one or more non-transitory computer media 34, and/or displayed on the display device 32. Once stored, the keyframes 36 can be access at any time by the user via the workstation 24. The comparison can include a comparison of a change in a number of features between the last-acquired keyframe 36 and the ultrasound images 19/camera images 21, a spatial shift of one of the ultrasound images 19 or one of the camera images, with the last-acquired keyframe, and so forth. In another example, the keyframe acquisition criterion 42 can include a recognition of a defining image feature of a target tissue imaged in a current ultrasound image 19 (e.g., the left or right ventricle, the left or right aorta, a specific blood vessel of a heart of the patient, such as the aorta or vena cava, and so forth). The comparison process can include a matching algorithm to match the feature sets 38 and 40 of the at least one ultrasound image 19 and the at least one camera image 21, respectively. Such algorithms can include, for example, using a sum of squared differences (SSD) algorithm. In some examples, a deformable registration algorithm known in the art that uses the feature sets 38 and 40 to improve matching between multiple keyframes 36. To increase the robustness of the keyframe matching, a sequence of the most recently-generated keyframes 36 are used in the matching process.

In an optional operation 106, the at least one electronic processor 28 is programmed to label, with a label 44, a keyframe 36 representative of the in vivo position of the ultrasound transducer 18 upon receiving a user input from a user via the at least one user input device 30 of the workstation 24. In one approach, the GUI 48 may provide a drop-down list GUI dialog of standard anatomical views (a midesophageal (ME) four chamber view, a ME (long axis (LAX) view, a transgastric (TG) Midpapillary short axis (SAX) view, among others) and the user can select one of the listed items as the label 44. Alternatively, a free-form text entry GUI dialog may be provided via which the user types in the label 44, or further annotates a label selected from a drop-down list. In addition, keyframes 36 can also be labeled as being indicative or representative of intermediate positions of the ultrasound transducer 18 (e.g., a position of the ultrasound transducer in a position between positions shown in "adjacent" ultrasound images 19 and/or camera images 21). In another example, a 2D or 3D visual representation of canonical views of the probe 12 can be shown, in which a current state of the probe is shown, while other, previously-acquired views of the probe can be selected for display by the user. The labels 44 and the labeled keyframes 36 can be stored in the one or more non-transitory computer readable media 34.

In some examples, rather than (or in addition to) employing manual labeling, the at least one electronic processor 28 can be programmed to label or otherwise classify the ultrasound images 19 and/or the camera images 21 according to particular anatomical views shown in the images (e.g., ME four chamber view, ME LAX view, TG Midpapillary SAX view, among others). The images 19 and 21 can be manually labelled by the user via the at least one user input device 30, or automatically labelled using ultrasound image matching algorithms known in the art.

Figure 4:
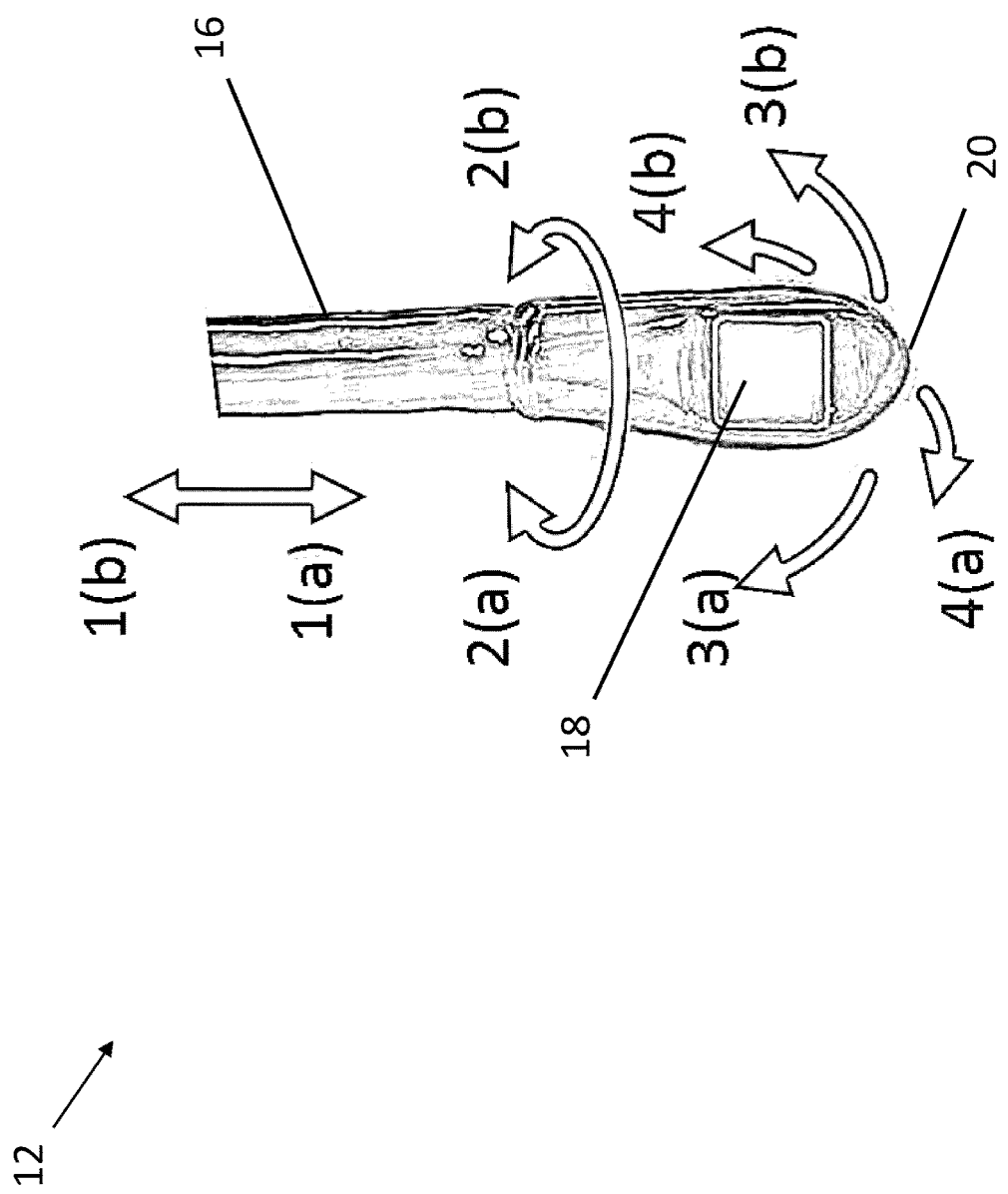
FIG. 4 shows potential moveable axes of the ultrasound device of FIGS. 1 and 2.

Referring briefly now to FIG. 4, and with continuing reference to FIGS. 1-3, the probe 12 is manipulatable (manually using knobs 27 or other manual manipulation, and/or robotically using servomotors 26, depending upon the embodiment) in a variety of manners. The probe 12 is able to advance along an "insertion" direction (i.e., into the esophagus) (labeled along an axis 1(a) in FIG. 3); and a "retraction" direction along an axis 1(b); rotate/turn along a forward angle direction along an axis 2(a), and rotate/turn along a back-angle direction along an axis 2(b). The distal end 16 of the probe 12 is configured to move (via user operation of the knobs 27) in an anterior/posterior flexion direction along an axis 3(*a*) and 3(*b*); a right/left direction along an axis 4(*a*) 4(*b*). The probe 12 can be moved along the axes 1(*a*), 1(*b*), 2(*a*), 2(*b*) by direct manipulation of the probe by a user, while movement along the axes 3(*a*), 3(*b*), 4(*a*), 4(*b*) using the knobs 27. These are illustrative degrees of freedom; a specific ultrasound probe implementation may provide more, fewer, and/or different degrees of freedom for manipulating the probe position in vivo, while subset of these degrees of freedom can be actuated manual, while others could be passively implemented.

Returning to FIGS. 1-3, in another optional operation 108, the at least one electronic processor 28 is programmed to guide (and, in the case of robotic embodiments, control) movement of the probe 12 through the esophagus via the construction of multiple keyframes 36. To do so, the at least one electronic processor 28 is programmed to construct a keyframe 36 that is representative of a first view consisting of a first in vivo position of the ultrasound transducer 18. During traversal of the ultrasound transducer 18 from the first view to a second view consisting of a second in vivo position of the ultrasound transducer, the at least one electronic processor 28 is programmed to construct keyframes 36 representative of "intermediate" positions of the ultrasound transducer (e.g., positions between the first and second views). In one example, these intermediate positions are implicitly included in the ultrasound and camera images 19, 21, in which case the probe 12 can be moved to match a target keyframe 36. In another example, the intermediate position can be an estimate of motion from one keyframe 36 to the next relative to an ultrasound volume, a camera image space, or a kinematic transformation in Cartesian or joint space, or a combination of any of these. At the end of the traversal of the ultrasound transducer 18, the at least one electronic processor 28 is programmed to construct a second keyframe 36 representative of the second view.

The operation 108 can include an operation in which the at least one electronic processor 28 is programmed to detect when a new keyframe 36 representative of the "intermediate positions" should be acquired and saved (i.e., during the transition from the first view to the second view). To do so, the most recently constructed keyframe 36 is compared to the most recently-acquired ultrasound images 19 and the most recently-acquired camera images 21. In one example if the number of features (e.g., anatomical features, and so forth) in the images 19, 21 changes in a way that exceeds a predetermined comparison threshold (25% of the features) as to the number of features in the keyframe 36, a new keyframe is generated. In another example, the average pixel displacement in the acquired images 19, 21 changes by a predetermined comparison threshold (e.g., x % of the image size) relative to the pixel displacement of the keyframe 36, then a new keyframe is generated. Other examples can include deformable matching algorithms known in the art to improve the images 19, 21 to image tracking. These thresholds can be empirically tuned.

In one example embodiment, the operation 108 is implemented in a manual mode. To do so, the at least one electronic processor 28 is programmed to provide human-perceptible guidance 46 during a manually executed (e.g. via knobs 27) backtracking traversal (i.e., "reverse" movement) of the ultrasound transducer 18 back from the second view to the first view (or to an intermediate view therebetween). The guidance 46 is based on comparisons of the ultrasound images 19 and the camera images 21 (acquired during backtracking traversal) with the keyframes 36 representative of the intermediate positions and the keyframe representative of the first view. The guidance 46 can include commands including one or more of: advancement of the ultrasound device 10 through the esophagus (e.g., "go forward and variants thereof); retraction of the ultrasound device through the esophagus (e.g., "reverse" and variants thereof), "turn," "capture a keyframe", and so forth. The guidance 46 can be output visually on the display device 32, audibly via a loudspeaker (not shown), and so forth. In addition, the guidance 46 can be displayed as overlaying the images 19 and 21 as displayed on the display device 32.

In another example embodiment, the operation 108 is implemented in an automated mode, in which the probe 12 is automatically moved through the esophagus by action of servomotors 26. To do so, the at least one electronic processor 28 is programmed to control the one or more servomotors 26 of the probe 12 to perform the traversal of the ultrasound transducer 18 from the first view to the second view. The at least one electronic processor 28 is then programmed to control the servomotors 26 of the probe 12 to perform a backtracking traversal of the ultrasound transducer 18 back from the second view to the first view based on comparisons of the ultrasound images 19 and the camera images 21 (acquired during the backtracking traversal) with the keyframes 36 representative of the intermediate positions, and the keyframe representative of the first view.

In both the manual mode and the automated mode, the at least one electronic processor 28 is programmed to guide the user in regard to the movement of the probe 12 through the esophagus by generating the GUI 48 for display on the display device 32. The user can use the GUI 48 to select a desired view or keyframe 36 using the at least one user input device 30. The desired view of keyframe 36 can include a keyframe that was previously-acquired and stored in the non-transitory computer readable medium 34, keyframes acquired during a current procedure, or predefined keyframes stored in the non-transitory computer readable medium. The matching algorithm for the image feature sets 38, 40 can be used to find a set of keyframes 36 that is closest to a current acquired keyframe as shown on the display device 30. For example, keyframes 36 from "view A" to "view N" are created by a user at the beginning of a procedure and saved in the non-transitory computer readable media 34. The views between adjacent views (e.g., "view A" to view "B", "view B" to "view C", and so forth) are linked using the "intermediate" keyframes 36. To do so, incremental motion between a current keyframe (e.g., "view B") and a next keyframe (e.g., "view C") using, for example, a motion estimation method such as a basic optical flow of features to estimate which way the probe 12 should move. The incremental motion direction that is required to move the probe 12 to the next keyframe to a desired view is implemented on the GUI 48. The incremental motion can be presented relative to, for example, a view of the camera 20, a view of the ultrasound transducer 18, a model of the probe 12, a model of the heart, a model of the patient, and so forth. The incremental motion can be shown, for example as a three-dimensional area indicated the direction of movement.

In some embodiments, once the desired final view is close, a beam forming-based image steering process can be used to obtain the desired final view.

In other embodiments, the knobs 27 can be used to alter the flexion and extension settings of the probe to a correlated data set of image features 38, 40 to improve the matching of keyframes 36 and the generated guidance 46. The knobs 27 can be manipulated (i.e., turned or switched), and the flexion and extension settings can be included in the GUI 48.

In further embodiments, the electronic processor 28 can robotically control the ultrasound probe 12 using the servomotors 26. By adding the keyframe 36 tracking and guidance 46 as feedback to the robotic control, a Cartesian velocity control loop can be used to smoothly and reliably move the probe 12 to the desired views. This allows for efficient, precise, and safe automatic positioning of the probe 12 between different views. In some embodiments, a forward kinematics pose of the robot can be used as another feature in the generation of the keyframes 36. In case of poor ultrasound image or camera image keyframe 36 matching, the prestored kinematic pose information can be used for transitioning to next keyframe.

In some embodiments, a data driven approach could be used for estimation of the current keyframe 36 relative to an atlas of keyframes (not shown) from many patients that is stored in the non-transitory computer readable media 34. This would enable guidance in patients without first seeing the desired views and building of the keyframes 36.

In other embodiments, a detection of adverse event can be shown on the GUI 48 such as, for example, when the sequence of images 19, 21 shows an image that is close to an expected camera image in a known sequence but contains new information, such as blood, or discoloration, or new anatomical topographical features like tear.

In some embodiments, an estimated motion of the probe 12 can be used for special volume stitching of multiple ultrasound images 38. In case of 3D data, it can provide excellent initialization information.

In further embodiments, a 3D model (not shown) can be created from poses of the probe 12 from the keyframe 36 locations with super-imposed ultrasound images 19. The user can select a particular keyframe 36 on the 3D model as a desired view, or for more information to review stored images 19 associated with that area.

In some embodiments, the probe 12 can include an integrated force sensing mechanism (not shown) that can be used for a variety of operations, including: recalling a desired view that involves pressure on the esophagus; maintaining contact and drift, limiting deformation on the esophagus to manage perforation risk; elastography, creating a 3D heat map of force loading regions of the esophagus or stomach.

Figure 5:
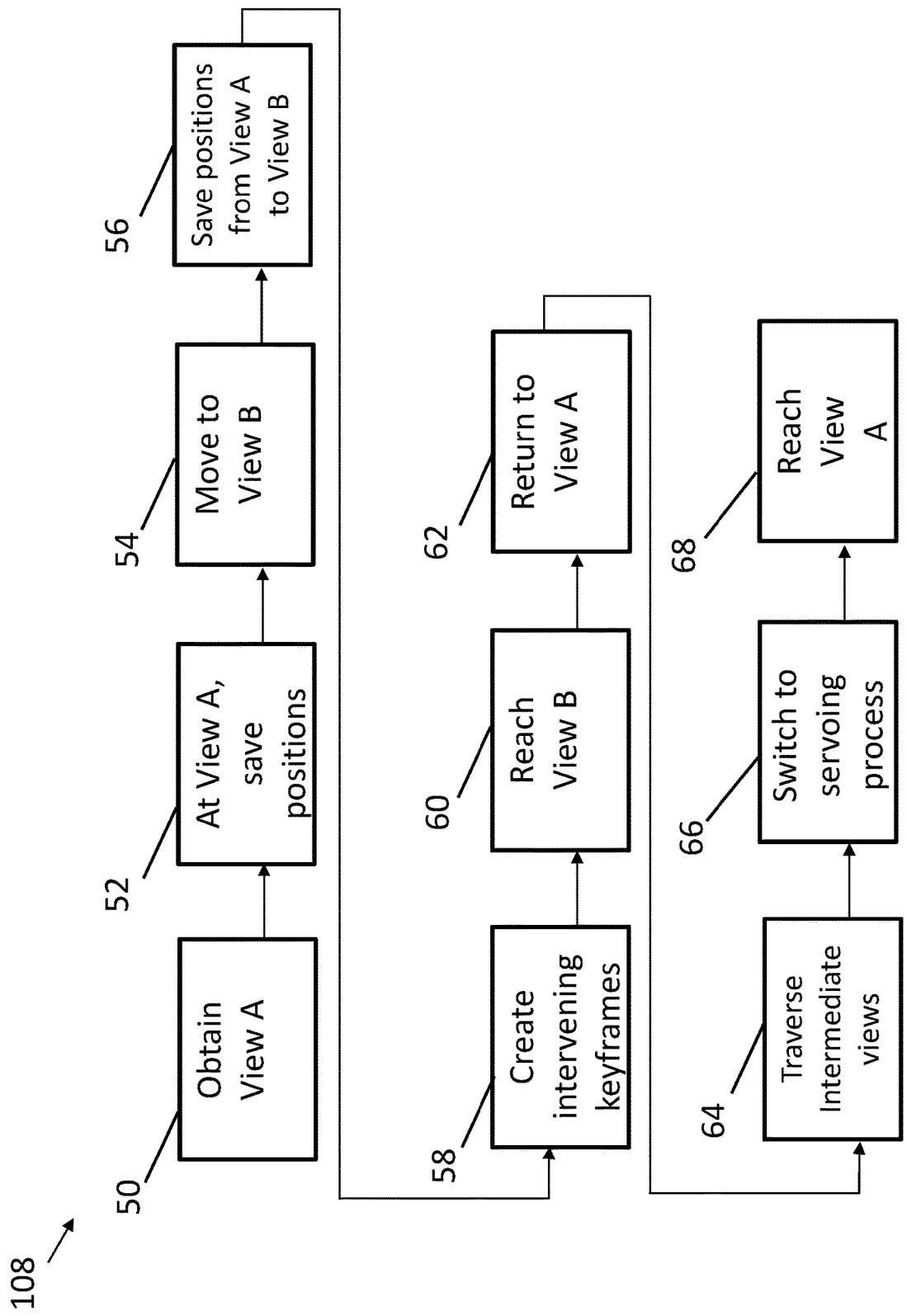
FIG. 5 shows another exemplary flow chart operations of the ultrasound device of FIGS. 1 and 2.

FIG. 5 shows an example flow chart of the movement operation 108. At an operation 50, a view labeled as "view A" of the probe 12 is acquired. At an operation 52, the positions of the ultrasound transducer 18, the camera 20, and any joint positions (not shown) of the probe 12 at View A are saved. At an operation 54, the probe 12 is moved from view A towards a new, desired view labeled as "View B." At an operation 56, the positions of the ultrasound transducer 18, the camera 20, and any joint positions (not shown) of the probe 12 as it moves from View A to View B. At an operation 58, intervening keyframes 36 having a change of 50% between View A and View B are created. At an operation 60, the probe 12 is moved until it reaches View B. At an operation 62, the probe 12 is moved from View B back towards View A using a visual servo on the GUI 48 in a reverse sequence of the intervening keyframes 36. At an operation 64, the probe 12 is move so as to traverse predefined intermediate views shown in the intervening keyframes 36. At an operation 66, when the probe 12 is near View A, the probe 12 is switched to an ultrasound-based servoing process. At an operation 68, the probe 12 is moved until it reaches View A. In addition to traversing from view B to A (e.g., operations 64, 66, and 68), keyframes 36 can be updated or added to the set describing the traversal from A to B and vice-versa. These can be used to enrich the resolution and richness of the keyframes 36.

Figure 6:
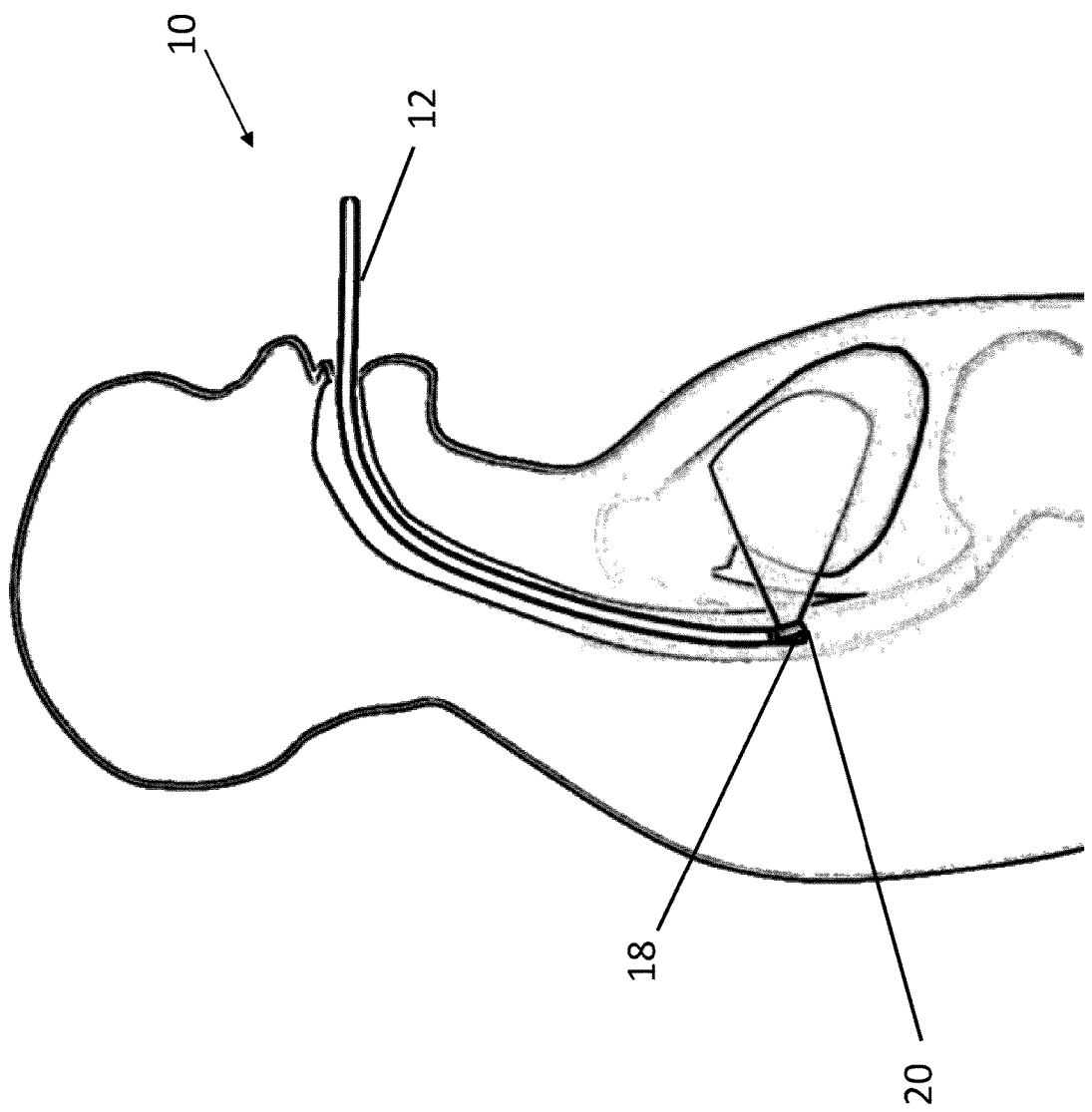
FIG. 6 shows an example use of the ultrasound device of FIGS. 1 and 2.

FIG. 6 shows an example use of the ultrasound device 10 inserted in vivo into a patient's esophagus. As shown in FIG. 6, the probe 12 is inserted down the esophagus of the patient so that the ultrasound transducer 18 and the camera 20 can acquire the respective ultrasound images 19 and the camera images 21 of the patient's heart. It will be appreciated that this is merely one specific application of the disclosed approaches for guiding a catheter-based ultrasound probe. For example, an Intracardiac Echo (ICE) or Intravascular Ultrasound (IVUS) probe can be analogously guided through a major blood vessel(s) of the patient to reach desired anatomical views, and to backtrack to a previous anatomical view.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. An ultrasound device, comprising:
 a probe including a tube sized for insertion into a patient and an ultrasound transducer disposed at a distal end of the tube;
 a camera mounted at the distal end of the tube in a fixed spatial relationship to the ultrasound transducer;
 at least one electronic processor programmed to:
  control the ultrasound transducer and the camera to acquire ultrasound images and camera images respectively while the ultrasound transducer is disposed in vivo inside the patient; and
  construct a keyframe representative of an in vivo position of the ultrasound transducer, wherein the keyframe is a single image and wherein the keyframe includes at least: (i) ultrasound image features extracted from at least one of the ultrasound images acquired at the in vivo position of the ultrasound transducer, wherein the keyframe further includes, displayed within the single image, one or more settings of the ultrasound transducer at the acquisition time of the ultrasound image acquired at the in vivo position of the ultrasound transducer; and (ii) camera image features extracted from one of the camera images acquired at the in vivo position of the ultrasound transducer; and
 a display configured to display the keyframe.

2. The ultrasound device of claim 1, wherein the keyframe further includes rotation settings, insertion settings, and joint position settings of the probe at the acquisition time of the ultrasound image acquired at the in vivo position of the ultrasound transducer.

3. The ultrasound device of claim 1, wherein the ultrasound transducer and the camera are attached to each other or housed in or secured to a common rigid housing disposed at the distal end of the tube.

4. The ultrasound device of claim 3, wherein the ultrasound transducer is arranged at the distal end of the tube to be side-emitting, and the camera is arranged at the distal end of the tube to be forward-facing.

5. The ultrasound device of claim 1, wherein the at least one electronic processor is programmed to construct the keyframe responsive to satisfaction of a keyframe acquisition criterion.

6. The ultrasound device of claim 5, wherein the keyframe acquisition criterion comprises a comparison between a last keyframe and currently acquired ultrasound and camera images.

7. The ultrasound device of claim 5, wherein the keyframe acquisition criterion comprises a recognition of a defining image feature of a target tissue imaged in a current ultrasound image.

8. The ultrasound device of claim 1, further including at least one user input device; and wherein the at least one electronic processor is programmed to:
label the keyframe representative of the in vivo position of the ultrasound transducer upon receiving a user input via the at least one user input device.

9. The ultrasound device of claim 1, wherein the at least one electronic processor is further programmed to:
construct a keyframe representative of a first view consisting of a first in vivo position of the ultrasound transducer;
during a traversal of the ultrasound transducer from the first view to a second view consisting of a second in vivo position of the ultrasound transducer, construct keyframes representative of intermediate positions of the ultrasound transducer; and
at the end of the traversal, construct a keyframe representative of the second view.

10. The ultrasound device of claim 9, wherein the at least one electronic processor is further programmed to:
during a backtracking traversal of the ultrasound transducer back from the second view to the first view or an intermediate view therebetween, provide human-perceptible guidance for manual control of the probe based on comparisons of ultrasound images and camera images acquired during backtracking traversal with the keyframes representative of the intermediate positions and the keyframe representative of the first view.

11. The ultrasound device of claim 10, wherein the human-perceptible guidance includes commands including one or more advancement of the ultrasound device through the esophagus, retraction of the ultrasound device through the esophagus, and capture a keyframe.

12. The ultrasound device of claim 9, wherein the at least one electronic processor is further programmed to:
control servomotors of the probe to perform the traversal of the ultrasound transducer from the first view to the second view; and
control the servomotors of the probe to perform a backtracking traversal of the ultrasound transducer back from the second view to the first view based on comparisons of ultrasound images and camera images acquired during the backtracking traversal with the keyframes representative of the intermediate positions and the keyframe representative of the first view.

13. The ultrasound device of claim 1, wherein the probe comprises a transesophageal echocardiography (TEE) probe.

14. An ultrasound device, comprising:
a probe including a tube sized for insertion into a patient and an ultrasound transducer disposed at a distal end of the tube and arranged to be side-emitting;
a camera mounted at the distal end of the tube in a fixed spatial relationship to the ultrasound transducer and arranged to be forward-facing;
at least one electronic processor programmed to:
control the ultrasound transducer and the camera to acquire ultrasound images and camera images respectively while the ultrasound transducer is disposed in vivo inside the patient; and
construct a keyframe representative of an in vivo position of the ultrasound transducer, wherein the keyframe is a single image and wherein the keyframe includes at least: (i) ultrasound image features extracted from at least one of the ultrasound images acquired at the in vivo position of the ultrasound transducer, further including one or more settings of the ultrasound transducer at the acquisition time of the ultrasound image acquired at the in vivo position of the ultrasound transducer; and (ii) camera image features extracted from one of the camera images acquired at the in vivo position of the ultrasound transducer; and
a display configured to display the keyframe.

15. The ultrasound device of claim 14, wherein the keyframe further includes one or more of:
one or more settings of the ultrasound transducer, rotation settings of the probe, insertion settings of the probe, and joint position settings of the probe at the acquisition time of the ultrasound image acquired at the in vivo position of the ultrasound transducer.

16. The ultrasound device of claim 14, wherein the at least one electronic processor is further programmed to:
construct a keyframe representative of a first view consisting of a first in vivo position of the ultrasound transducer;
during a traversal of the ultrasound transducer from the first view to a second view consisting of a second in vivo position of the ultrasound transducer, construct keyframes representative of intermediate positions of the ultrasound transducer; and
at the end of the traversal, construct a keyframe representative the second view.

17. The ultrasound device of claim 16, wherein the at least one electronic processor is further programmed to:
during a backtracking traversal of the ultrasound transducer back from the second view to the first view, provide human-perceptible guidance for manual control of the probe based on comparisons of ultrasound images and camera images acquired during backtracking traversal with the keyframes representative of the intermediate positions and the keyframe representative of the first view.

18. The ultrasound device of claim 16, wherein the at least one electronic processor is further programmed to:
control servomotors of the probe to perform the traversal of the ultrasound transducer from the first view to the second view; and
control the servomotors of the probe to perform a backtracking traversal of the ultrasound transducer back from the second view to the first view based on comparisons of ultrasound images and camera images acquired during the backtracking traversal with the keyframes representative of the intermediate positions and the keyframe representative of the first view.

19. A method of controlling an ultrasound device comprising a probe including a tube sized for insertion into a patient and an ultrasound transducer disposed at a distal end of the tube and a camera mounted at the distal end of the tube in a fixed spatial relationship to the ultrasound transducer, the method comprising:
controlling the ultrasound transducer and the camera to acquire ultrasound images and camera images respectively while the ultrasound transducer is disposed in vivo inside the patient;

constructing a keyframe representative of a first view consisting of a first in vivo position of the ultrasound transducer, wherein the keyframe is a single image and wherein the keyframe includes including at least: (i) the ultrasound images, (ii) the camera images, (iii) ultrasound image features extracted from at least one of the ultrasound images acquired at the in vivo position of the ultrasound transducer further including one or more settings of the ultrasound transducer at the acquisition time of the ultrasound image acquired at the in vivo position of the ultrasound transducer; and (iv) camera image features extracted from one of the camera images acquired at the in vivo position of the ultrasound transducer;

during a traversal of the ultrasound transducer from the first view to a second view consisting of a second in vivo position of the ultrasound transducer, constructing keyframes representative of intermediate positions of the ultrasound transducer; and at the end of the traversal, constructing a keyframe representative the second view.

* * * * *